US008357372B2

(12) United States Patent
Williams et al.

(10) Patent No.: US 8,357,372 B2
(45) Date of Patent: *Jan. 22, 2013

(54) AGENT FOR TREATING ALLERGIC OR HYPERSENSITIVITY CONDITION

(75) Inventors: Neil Andrew Williams, Axbridge (GB); Timothy Raymond Hirst, Clevedon (GB); John Bienenstock, Toronto (CA)

(73) Assignee: Trident Pharmaceuticals, Inc., Boston, MA (US)

( * ) Notice: Subject to any disclaimer, the term of this patent is extended or adjusted under 35 U.S.C. 154(b) by 807 days.

This patent is subject to a terminal disclaimer.

(21) Appl. No.: 11/691,798

(22) Filed: Mar. 27, 2007

(65) Prior Publication Data

US 2008/0206284 A1   Aug. 28, 2008

Related U.S. Application Data

(63) Continuation of application No. 09/600,060, filed as application No. PCT/GB99/00070 on Jan. 8, 1999, now Pat. No. 7,208,155.

(30) Foreign Application Priority Data

Jan. 9, 1998   (GB) .................................. 9800487.2

(51) Int. Cl.
*A61K 39/40* (2006.01)
*A61K 39/108* (2006.01)
*A61K 38/16* (2006.01)

(52) U.S. Cl. ...................... 424/184.1; 424/241.1; 514/12

(58) Field of Classification Search ........................ None
See application file for complete search history.

(56) References Cited

U.S. PATENT DOCUMENTS

| 5,614,611 | A | 3/1997 | Chang |
| 5,681,571 | A | 10/1997 | Holmgren et al. |
| 7,097,845 | B2 * | 8/2006 | Petersen .................... 424/236.1 |
| 7,208,155 | B1 * | 4/2007 | Williams et al. ........... 424/184.1 |
| 7,588,763 | B2 * | 9/2009 | Williams et al. ........... 424/184.1 |
| 2001/0036917 | A1 * | 11/2001 | Williams et al. ................... 514/3 |
| 2006/0083751 | A1 * | 4/2006 | Williams et al. ........... 424/185.1 |

FOREIGN PATENT DOCUMENTS

| WO | WO 91/12818 | 9/1991 |
| WO | WO 97/02045 | 1/1997 |
| WO | WO 98/47529 | 10/1998 |
| WO | WO 95/10301 | 4/1999 |

OTHER PUBLICATIONS

Aman et al., Proc Natl Acad Sci USA 98(15):8536-8541, Jul. 2001.
Herz et al., Methods 32(3):271-80, Mar. 2004.
Holmgren, J., et al., Proc. Natl. Acad. Sci. USA 72:2520-2524, 1975.
Holmgren J, Strategies for the induction of immune responses at mucosal surfaces making use of cholera toxin B subunit as immunogen, carrier, and adjuvant Am J Trop Med hyg 1994 50(5 Suppl): 42-54. Abstract.
Hoynes et al., Immunology and Cell Biology 74:180-186, 1996.
Hirai et al, Microbial Immunol 44(4);259-66,2000.
Kagan et al, Environ Health Perspect 111(2)223-5, Feb 2003.
Kim et al., Cholera Toxin and Cholera Toxin B Subunit Induce IgA SwitchingThrough the Action of TGF betal, Feb. 1998, J. Immunology 160(3): 1198-1203.
Marinaro et al., J. Immunology 155:4621-4629, 1995.
Nashar, T.O., et al., Immunology 91:572-578 (1997).
Nashar, T.O., et al., Proc. Natl. Acad. Sci. USA 93:2226-230, 1996.
Okahashi et al., Infection and Immunity 64(5):15161524, May 1996.
Patterson et al., J. Immunol 117(1):97-101, Jul. 1976.
Roitt et al., in Immunology, $2^{nd}$ Edition, pp. 19.1-19.3, 1989.
Snider et al., J. Immunology 153:647-657, 1994.
Takabayashi et al., J. Immunology 170:3898-3905, 2003.
Wiedermann et al., International Immunology 11(7):1131-38, 1999.
Tamura et al., Vaccine 15(2):225-229, 1997.
Williams et al., Proc. Natl. Acad. Sci. USA 94:5290-5295, May 1997.
Yamamoto et al., Mutants in the ADP-ribosyltransferase Cleft of Cholera Toxin lack darrheagenicity but retain adjuvanticity, Apr. 1997, J. Exp. Med. 185(7): 1203-1210.
Yankelevich, B., et al., J. Immunology 154:3611-3617 (1995).
Bergerot et al., "A cholera toxoid-insulin conjugate as an oral vaccine against spontaneous autoimmune diabetes", *Proc. Natl. Acad. Sci. U.S.A.*, 94:4610-4614 (1997).
Bienenstock, J., "The Physiology of the Local Immune Response and the Gastrointestinal Tract", *Progress in Immunology II, vol. 4 Clinical Aspects*, I.L. Brent, J. Holborrow, Eds., Amsterdam, Holland, pp. 197-207 (1974).
Czerkinsky et al., "Exploration of Mucosal Immunity in Humans: Relevance to Vaccine Development", *Cell. Mol. Biol.*, 40(Suppl. 1):37-44 (1994).
Definition of "ganglioside" in *Oxford Dictionary of Biochemistry and Molecular Biology*, Smith et al., Eds., Oxford University Press, New York, NY, p. 254 (1997).
Elson et al., "Cholera Toxin Feeding Did Not Induce Oral Tolerance in Mice and Abrogated Oral Tolerance to an Unrelated Protein Antigen", *J. Immunol.*, 133(6):2892-2897 (1984).
Jetborn et al., "Safety and immunogenicity of an oral recombinant cholera B subunit-whole cell vaccine in Swedish volunteers", *Vaccine*, 10(2):130-132 (1992).
Lehninger, A. L., Biochemistry, 2nd Ed., Worth Publishers, Inc., New York, pp. 294-295 (1975).
Lycke et al., "Strong adjuvant properties of cholera toxin on gut mucosal immune responses to orally presented antigens", *Immunol.*, 59:301-308 (1986).
Merritt et al., "Crystal structure of cholera toxin B-pentamer bound to receptor GM1 pentasaccharide", *Protein Science*, 3:166-175 (1994).
Nashar et al., "Cross-linking of cell surface ganglioside GM1 induces the selective apoptosis of mature CD8+ T lymphocytes", *Intl. Immunol.*, 8(5):731-736 (1996).

(Continued)

*Primary Examiner* — Phuong Huynh
(74) *Attorney, Agent, or Firm* — Mintz Levin Cohn Ferris Glovsky and Popeo, P.C.; Ivor R. Elrifi; Jennifer L. Loebach

(57) ABSTRACT

The use of an agent in the manufacture of a medicament to affect an allergic condition and/or a hypersensitivity condition is described. The agent is capable of modulating a ganglioside associated activity. The agent is not coupled to an antigen. The modulation of the ganglioside activity affects an allergic condition and/or a hypersensitivity condition.

4 Claims, No Drawings

OTHER PUBLICATIONS

Nashar et al., "Current progress in the development of the B subunits of cholera toxin and *Escherichia coli* heat-labile enterotoxin as carriers for the oral delivery of heterologous antigens and epitopes", *Vaccine*, 11(2):235-240 (1993).

Nashar et al., "Potent immunogenicity of the B subunits of *Escherichia coli* heat-labile enterotoxin: Receptor binding is essential and induces differential modulation of lymphocyte subsets", *Proc. Natl. Acad. Sci. U.S.A.*, 93:226-230 (1996).

Ruedl et al., "Humoral and cellular immune responses in the murine respiratory tract following oral immunization with cholera toxin or *Escherichia coli* heat-labile enterotoxin", *Vaccine*, 14 (8): 792-798, 19798, 1996.

Sixma et al., "Lactose binding to heat-labile enterotoxin revealed by X-ray crystallography", *Nature*, 355:561-564 (1992).

Sun et al., "Cholera toxin B subunit: An efficient transmucosal carrier-delivery system for induction of peripheral immunological tolerance", *Proc. Natl. Acad. Sci. U.S.A.*, 91:10795-10799 (1994).

Sun et al., "Treatment of experimental autoimmune encephalomyelitis by feeding myelin basic protein conjugated to cholera toxin B subunit", *Proc. Natl. Acad. Sci. U.S.A.*, 93:7196-7201 (1996).

Svennerholm, L., "Interaction of Cholera Toxin and Ganglioside GM1", *Adv. Exp. Med. Biol.*, 71:191-204 (1976).

Umesaki et al., "Immune responses of mice to orally administered asialo GM1-specific rabbit IgG in the presence or absence of cholera toxin", *Immunol.*, 75:386-388 (1992).

* cited by examiner

AGENT FOR TREATING ALLERGIC OR HYPERSENSITIVITY CONDITION

RELATED APPLICATIONS

This patent application is a continuation of U.S. patent application Ser. No. 09/600,060, filed Jul. 10, 2000, which issued as U.S. Pat. No. 7,208,155 on Apr. 24, 2007, which is a national stage application of PCT/GB99/00070, filed Jan. 8, 1999 which claims the benefit of GB 9800487.2, filed Jan. 9, 1998. All of which are hereby incorporated by reference in their entirety.

FIELD OF INVENTION

The present invention relates to a medicament.

In particular, the present invention relates to a medicament useful to affect an allergic condition and/or a hypersensitivity condition.

More in particular, in one aspect the present invention relates to an immunological tolerance inducing agent.

More in particular, the present invention relates to such an agent optionally co-administered with a specific antigen for use in the treatment of mammalian particularly human, allergic and other hypersensitivity diseases.

BACKGROUND

When an adaptive immune response occurs in an exaggerated or inappropriate form, the term allergy or hypersensitivity is applied. Allergic or hypersensitivity reactions are the result of normally beneficial immune responses acting inappropriately to foreign antigens (usually environmental macromolecules) and sometimes cause inflammatory reactions and tissue damage. In these situations, a normally harmless environmental stimulus, called an "allergen", triggers an immune response which upon re-exposure, is re-activated to generate pathological damage. Allergies or hypersensitivities are distinguished into four types of reactions. The first three are antibody-mediated, the fourth is mediated mainly by T cells and macrophages.

In Type I Immediate Hypersensitivity/Atopic Allergy, the principal immune response to the allergen involves the production of IgE antibodies. Such disorders are by far the most prevalent in humans and are seen as principal targets for new therapeutic approaches. Although these diseases are not exclusively IgE mediated, IgE binds to cells within the tissues such as mast cells and basophils and the cross-linking of IgE on the cells surfaces by allergen invokes the release of many inflammatory mediators.

Typical examples of such diseases include asthma, allergic cough, allergic rhinitis and conjunctivitis, atopic eczema and dermatitis, urticaria, hives, insect bite allergy, dietary and certain drug allergies. In many cases, the particular allergens are known. By way of example, the principal allergen in asthma is DerP1 from house dust mite but other triggers of asthma such as pet dander antigens also exist.

Type II or antibody dependent cytotoxic hypersensitivity occurs when antibodies of a different type, usually IgG and IgM, binds to either self antigen or foreign antigen on cells and leads to phagocytosis, killer cell activity or complement mediated lysis. These types of allergies are relatively unusual but can include some allergies to drugs.

Type III hypersensitivity develops when immune complexes are formed in large quantities or cannot be cleared adequately by the reticuloendothelial system. The immune complexes usually result from the deposition of antibody, usually IgM or IgG, allergen complexes at these sites. In normal circumstances, antibody binds to allergen and is cleared by a variety of tissue cells. However, a number of factors may influence the persistence of the immune complexes and where they remain in the blood for prolonged periods, they can lodge and establish inflammation in the kidneys, skin (where they cause rashes) and joints (where they can cause a type of arthritis other than rheumatoid arthritis).

Type IV or delayed type hypersensitivity (DTH) does not involve antibody but instead the prolonged activation of T lymphocytes. These T cells are capable of secreting soluble factors causing tissue damage and enhancing the recruitment and activation of other cell types to the tissues. Incoming cells themselves contribute to the inflammation and tissue damage. DTH is most seriously manifested when antigens (for example those associated with *mycobacteria tuberculosis*) are trapped in a macrophage and cannot be cleared. T cells are then stimulated to elaborate cytokines which mediate a range of inflammatory responses. DTH reactions are less common than Type I reactions but are seen in graft rejection and allergic contact dermatitis which is generally manifested as a contact sensitivity (allergy usually involving skin rash) to environmental "contact allergens" such as heavy metals.

Oral administration of antigens—such as allergens and autoantigens—has long been recognised as a method to prevent peripheral T cell responses and, in the case of autoantigens, has also been shown to prevent or delay the onset of several experimental autoimmune diseases including experimental allergic encephalomyelitis (EAE). Major problems recognised with such strategies are that it usually requires feeding of large, if not massive, doses of autoantigens and it is generally less efficient in an immune as opposed to a naive host. The latter problem has limited the therapeutic potential of this strategy. However, it has now been shown by Sun et al (1994 Proc Natl Acad Sci 91: 10795-10799) that oral administration of minute amounts of prototype particulate and soluble protein antigens conjugated to cholera toxin B subunit (CtxB), the nontoxic receptor-binding moiety of cholera toxin, can readily induce tolerance in the peripheral T-cell compartment and is effective not only in naive but also in systemically sensitised animals. In addition, oral administration of minute amounts of an autoantigen, myelin basic protein (MBP), coupled to CtxB can prevent EAE in Lewis rats (Sun et al 1996 Proc Natl Acad Sci 93: 7196-7201). Other researchers have also shown that feeding even a single dose of minute amounts (microgram) of antigens conjugated to the receptor binding nontoxic B subunit moiety of cholera toxin (CtxB) can markedly suppress systemic T cell mediated inflammatory reactions in naive as well as in experimental animals (Bergerot et al 1997 Proc Natl Acad Sci 94: 4610-4614).

*Escherichia coli* (*E. coli*) heat labile enterotoxin (Etx) and its closely related homologue, cholera toxin (Ctx), are examples of protein toxins which bind to glycolipid receptors on host cell surfaces. Each toxin consists of six noncovalently linked polypeptide chains, including a single A subunit (27 kDa) and five identical B subunits (11.6 kDa) which principally bind to GM1 ganglioside receptors found on the surfaces of mammalian cells (Nashar et al 1996 Proc Natl Acad Sci 93: 226-230). The A subunit is responsible for toxicity possessing adenosine diphosphate (ADP) ADP-ribosyltransferase activity, whereas the B subunits (EtxB and CtxB) are non-toxic oligomers which bind and cross-link a ubiquitous cell surface glycolipid ganglioside, called GM1, thus facilitating A subunit entry into the cell.

The GM1 ganglioside receptor is a member of family of gangliosides comprising sialic acid containing glycolipids (also called glycosphingolipids) which are formed by a hydrophobic portion, the ceramide, and a hydrophilic part, that is the oligosaccharide chain. Gangliosides are defined as any ceramide oligosaccharide carrying, in addition to other sugar residues, one or more sialic residues (Oxford Dictionary of biochemistry and molecular biology. Oxford University Press. 1997. Eds Smith A D, Datta S P, Howard Smith G, Campbell P N, Bentley R and McKenzie H A). Although first described in neural tissue, several studies have shown that gangliosides are almost ubiquitous molecules expressed in all vertebrate tissues. Within cells, gangliosides are usually associated with plasma membranes, where they may act as receptors for a variety of molecules and take part in cell-to-cell interaction and in signal transduction. In addition, gangliosides are expressed in cytosol membranes like those of secretory granules of some endocrine cells such as the pancreatic islets and adrenal medulla.

Gangliosides contain in their oligosaccharide head groups one or more residues of a sialic acid which gives the polar head of the gangliosides a net negative charge at pH 7.0. The sialic acid usually found in human gangliosides is N-acetylneuraminic acid. Over 20 different types of gangliosides have been identified, differing in the number and relative positions of the hexose and sialic residues which form the basis of their classification. Nearly all of the known gangliosides have a glucose residue in glycosidic linkage with ceramide, residues of D-galactose and N-acetyl-D-galactosamine are also present.

In the ganglioside nomenclature of gangliosides, devised by Svennerholm (Biochemistry Lehninger 2nd Ed 1975 Worth Publishers Inc p 294-295), the subscript letters indicate the number of sialic groups. M is monosialo, D is disialo and T is trisialo.

One of the best studied members of the ganglioside family is the monosialosylganglioside, GM1, which has been shown to be the natural receptor for the cholera toxin. Soluble ganglioside GM1 binds to the toxin with high affinity and inactivates it (Svennerholm 1976 Adv Exp Med Biol 71: 191-204).

The chemical formula for GM1 can be represented as:

Gal β3GalNAc β4(NeuAc alpha 3)Gal β4Glc β1 Cer where Glc is D-glucose, Gal is D-galactose, GalNAc is N-acetyl-D-galactosamine; NeuAc is N-acetylneuraminic acid, Cer is ceramide.

The chemical formula for GM1 can also be represented as galactosyl-N-acetylgalactosaminyl {sialosyl} lactosyl ceramide or galactosyl-N-acetyl-galactosaminyl-(sialyl)-galactosylglusosylceramide The x-ray crystal structures of Etx bound to lactose (Sixma et al 1992 Nature (London) 355: 561-564) and CtxB bound to the pentasaccharide of GM1 (Merritt et al 1994 Protein Sci 3: 166-175) have revealed that CtxB and EtxB bind to the terminal galactose and sialic acid moieties of GM1 which can be represented as Galβ-1-3-3GalNAc and that such binding does not induce any striking changes in B subunit conformation.

Furthermore the cholera toxin has been shown to demonstrate an absolute requirement for terminal galactose and internal sialic acid residues (as in GM1) with tolerance for substitution with a second internal sialic acid (as in GD1b).

Etx, like Ctx also probably binds to the terminal sugar sequence

Gal β1-3GalNAc β1-4(NeuAc alpha 2-3)Gal where GalNAc is the N-acetylgalactosamine and NeuAc is N-acetylneuraminic acid.

In addition to binding to GM1, EtxB binds weakly to other gangliosides, including non-galactose containing GM2 and asialo-GM1 as well as galactoproteins (Nashar et al Immunology 1997 91: 572-578). Other researchers have shown that EtxB is capable of binding to GM1 and tolerated removal or extension of the internal sialic acid residue (as in asialo-GM1 and GD1b respectively) but not substitution of the terminal galactose of GM1 (Umesaki and Setoyama 1992 Immunology 75: 386-388).

In contrast to the poor immunogenicity of the A subunit alone, both EtxB and CtxB are exceptionally potent immunogens and their respective holotoxins, Etx and Ctx, are known to be exceptionally potent adjuvants when given orally in combination with unrelated antigens (Ruedl et al 1996 Vaccine 14: 792-798; Nashar et al 1993 Vaccine 11: 235; Nashar and Hirst 1995 Vaccine 13: 803; Elson and Ealding 1984 J Immunol 133: 2892; Lycke and Holmgren 1986 Immunology 59: 301). Because of their remarkable immunogenicity, both EtxB and CtxB have been used as carriers for other epitopes and antigens (Nashar et al 1993 ibid) and have been used as components of vaccines against cholera and E. coli diarrhoea (Jetborn et al 1992 Vaccine 10: 130).

The ability of the B subunit of Ctx and Etx to interact with receptors present on mammalian cells has been shown to exert modulatory effects on the function of those cells. It is known that cells of the immune system are differentially affected following such interaction. In particular, WO 95/020045 discloses that EtxB binds to GM1 ganglioside receptors which are found on the surfaces of mammalian cells and that this binding induces differential effects on lymphocyte populations including a specific depletion of CD8+ T cells and an associated activation of B cells. These effects are absent when a mutant EtxB protein lacking GM1 binding activity is employed. These observations have led to the use of agents capable of binding to GM1 in the prevention and treatment of autoimmune disease, transplant rejection and graft versus host disease (GVHD). These studies suggest that agents that bind to GM1 or mimic binding to GM1 promote the induction of immunological tolerance.

Researchers have shown that a state of immunological unresponsiveness, also known as "immunological or oral tolerance", can be induced by the oral administration of dietary protein antigens. (Sun et al 1994 ibid; Sun et al 1996 ibid, Bergerot et al 1997 ibid). The inhalation of antigens can also induce a state of specific immunological unresponsiveness or "nasal tolerance". Thus, systemic immunological tolerance can be induced when antigen is administered orally or nasally by a mucosal route. WO 95/01301 discloses an immunological tolerance-inducing agent comprising a mucosa-binding agent linked to a specific tolerogen. WO95/10301 also includes mention of the treatment of allergy using a mucosa binding agent coupled to an allergen. Other researchers such as Tamura et al (1997 Vaccine 15: 225-229) have taken directly the protocol of WO 95/10301 and tested its efficacy in preventing allergy in a murine model of Type I allergy. They reported a significant lowering of IgE levels which are a strong predictor of efficacy and they cite data, following administration of EtxB coupled to ovalbumin (the results were not included), which shows that EtxB was not effective once IgE levels are established. It has also been shown that orally administered Ctx and Etx can act on several humoral and cellular immune responses not only at the gastrointestinal tract, but also in distant mucosal effector sites such as the respiratory tract. These data suggest that these mucosal adjuvants have a potential use in oral immunisation strategies to improve the local immune responses in remote mucosal tissues, in accordance with the concept of a common mucosal immune system (Bienenstock J 1974 The physiology of the local immune system and the gastrointestinal tract. In: Progress in Immunology II, vol 4: clinical aspects, I. L. Brent, J. Holborrow, Eds. Amsterdam, North Holland, pp197-207; Ruedl et al 1996 ibid; Umesaki 1992 ibid; Czerkinsky and Holmgren (1994 Cell Mol Biol 40: 3744).

The induction of immunological tolerance may include a number of different mechanisms which may be summarised as follows:
  (i) a process whereby antigen reactive cells are removed through triggering them to commit suicide (apoptosis);
  (ii) an induction of anergy or the long term inactivation of the antigen reactive cells;
  (iii) immune deviation of the antigen reactive cells away from the production of pathological responses;
  (iv) suppression of the antigen reactive cells or their regulation by specific factors or regulatory cells In the treatment of allergy, it is possible that the induction of any of these mechanisms may be useful. However, while the deletion of antigen reactive cells and/or the induction of anergy are useful strategies once the precise allergens are known, invoking these mechanims will usually silence only those cells which respond to the allergen which was given in the treatment regime. On the other hand, the implementation of immune deviation or suppression strategies has the advantage of potential regulation of responses to antigens which are involved in the condition but were not part of the treatment. This phenomenon, known as "bystander suppression" allows the "spread" of tolerance to other antigens (such as allergens) in the target tissues through either the possible secretion of non-antigen specific suppressor molecules or through suppressive cellular interactions in that tissue as a result of the interaction between the antigen specific cells and the specific immunising antigen. In this way, as long as at least one of the antigens involved in the disorder is known, the condition may be treated even if there are other antigens implicated as well. Thus, the goal of a good treatment is the induction of a specific immune deviation or suppression.

Nashar and co-workers (Proc Natl Acad Sci 1996 93: 223-226; Int Immunol 1996 8: 731-736; Immunol 1997 91: 572-578) have demonstrated that the administration of EtxB and other homologues can modulate the immune response away from the production of Th1 cytokines such as IFNγ and interleukin 2 (IL-2) and towards the secretion of Th2 cytokines such as IL-4, IL-10 and IL-13. IFNγ is the classical Th1 cytokine, IL-4 is the classical Th2 cytokine. This "immune deviation" is the basis of the disclosure in WO 97/02045 and has been shown to be effective in the treatment of autoimmune diseases. The experimental results in WO 97/02045 would suggest that GM1 binding agents would not find use in the treatment of allergic conditions and/or hypersensitivity conditions since such conditions involve IgE, the production of which is generally accepted to be promoted by IL-4 and down regulated by IFNγ.

The present invention now seeks to provide new ways of treating allergic conditions and/or hypersensitivity conditions through the induction of a specific immune deviation or suppression.

SUMMARY OF THE INVENTION

According to a first aspect of the present invention, there is provided the use of an agent in the manufacture of a medicament to affect an allergic condition and/or a hypersensitivity condition; wherein the agent is capable of modulating a ganglioside associated activity; wherein the agent is not coupled to an antigen; and wherein the modulation of the ganglioside associated activity affects an allergic condition and/or a hypersensitivity condition.

According to a second aspect of the present invention, there is provided the use of an agent in the manufacture of a medicament to affect an allergic condition and/or a hypersensitivity condition; wherein the agent is capable of modulating a GM1 associated activity; wherein the agent is not coupled to an antigen; and wherein the modulation of the GM1 associated activity affects an allergic condition and/or a hypersensitivity condition.

According to a third aspect of the present invention, there is provided an agent according to the present invention capable of blocking an IgE mediated response.

Preferably, the agent is capable in vivo of blocking an IgE mediated response.

According to a fourth aspect of the present invention, there is provided an assay method for identifying an agent according to the present invention capable of affecting an allergic condition and/or a hypersensitivity condition; wherein the assay method comprises: (a) contacting an agent with a ganglioside; (b) determining whether the agent modulates a ganglioside associated activity; such that the modulation of the ganglioside associated activity is indicative that the agent may be capable of affecting an allergic condition and/or a hypersensitivity condition; and wherein the agent is not coupled to an antigen.

According to a fifth aspect of the present invention, there is provided an assay method according to the present invention wherein the assay is an assay to screen for an agent useful in the prevention and/or treatment of an allergic condition and/or a hypersensitivity condition.

According to a sixth aspect of the present invention, there is provided a process comprising the steps of: (a) performing the assay according to the present invention; (b) identifying one or more agents capable of modulating a ganglioside associated activity; and (c) preparing a quantity of those one or more agents.

According to a seventh aspect of the present invention, there is provided a process comprising the steps of: (a) performing the assay according to the present invention; (b) identifying one or more agents capable of modulating a ganglioside associated activity; and (c) preparing a pharmaceutical composition comprising those one or more identified agents.

According to an eighth aspect of the present invention, there is provided a process comprising the steps of: (a) performing the assay according to the present invention; (b) identifying one or more agents capable of modulating a ganglioside associated activity; and (c) modifying one or more identified agents capable of modulating a ganglioside associated activity; and (d) preparing a pharmaceutical composition comprising those one or more modified agents.

According to a ninth aspect of the present invention, there is provided an agent identified by the process of the present invention.

Preferably the agent identified had not previously been known to affect an allergic condition and/or a hypersensitivity condition through modulation of a ganglioside associated activity.

According to a tenth aspect of the present invention, there is provided a method of affecting an allergic condition and/or a hypersensitivity condition with one or more agents; wherein the agent is capable of modulating a ganglioside associated activity in an in vitro assay method; and wherein the in vitro assay method is the assay method defined in the present invention.

Preferably there is provided a method of affecting in vivo an allergic condition and/or a hypersensitivity condition with one or more agents; wherein the agent is capable of modulating a ganglioside associated activity in an in vitro assay method; and wherein the in vitro assay method is the assay method defined in the present invention.

According to a eleventh aspect of the present invention, there is provided an agent according to the present invention for use as a pharmaceutical.

According to a twelfth aspect of the present invention, there is provided the use of an agent according to the present invention in the manufacture of a medicament to affect an allergic condition and/or a hypersensitivity condition.

According to a thirteenth aspect of the present invention, there is provided a pharmaceutical composition comprising or prepared from an agent according to the present invention.

Preferably the agent is a GM1 binding agent.

Preferably, the agent capable of modulating a ganglioside associated activity is selected from a group consisting of Ctx, Etx, CtxB and EtxB.

Preferably, the agent capable of modulating a ganglioside associated activity is capable of blocking an IgE mediated response in a subject with an allergic condition and/or a hypersensitivity condition.

Preferably the subject is a human—e.g. a human patient.

Preferably the agent is EtxB.

In a particularly preferred embodiment the agent is the wild type EtxB.

Alternatively, preferably the agent is either a mutant of EtxB which is capable of modulating a ganglioside associated activity or other equivalent proteins thereof.

Preferably the agent(s) is/are non-toxic.

Preferably the agent is CtxB and mutants thereof which are capable of modulating a ganglioside associated activity.

Preferably the ganglioside is a GM1 ganglioside receptor.

Preferably the agent capable of modulating a ganglioside associated activity is capable of cross-linking GM1 ganglioside receptors.

Preferably EtxB is one such agent which is capable of cross-linking GM1 ganglioside receptors by virtue of its pentameric form.

Preferably the medicament is used for the treatment or prophylaxis of a Type I allergic and/or a Type IV hypersensitivity condition such as contact hypersensitivity.

Preferably the medicament includes one or more antigens which are optionally co-administered with antigen.

Preferably the agent may be administered to a mammal with or without co-administration of an antigen.

Preferably the mammal is a human—e.g. a human patient.

DETAILED DESCRIPTION

In accordance with the present invention we have surprisingly found that the use of agents capable of modulating a ganglioside associated activity, when given alone or when co-administered with suitable antigens, can be used as an effective treatment for allergic and/or hypersensitivity conditions. Previous workers have either not attempted to find a mechanism (Sun et al 1996 ibid) or have argued that agents capable of modulating a ganglioside associated activity, such as EtxB and CtxB, cause a Th1 to Th2 switch in the immune response to antigen (WO97/02045). Since allergic conditions are known in the art to be promoted by Th2 responses, then the previous findings suggest that such agents would either be ineffective in treating allergies or may even worsen them.

We have surprisingly found that while EtxB and CtxB promote some aspects of Th2-associated responses, in some cases, they may not stimulate the production of the key factor in triggering allergy, IgE. Thus allergic conditions and/or hypersensitivity conditions can be treated with an agent capable of modulating a ganglioside associated activity, for instance, which is not coupled with an antigen.

Significantly, the linkage of the components was not found to be necessary. Furthermore, our findings indicate that the mechanisms of protection against allergic conditions and/or hypersensitivity conditions may include, though not be limited to either the suppression of antigen specific IgE secretion and/or the upregulated production of non-inflammatory antigen specific antibody isotypes (particularly IgG and IgA).

Thus, the present invention is advantageous because allergic conditions and/or hypersensitivity conditions can be treated with an agent capable of modulating a ganglioside associated activity which is optionally co-administered with an antigen.

The term "ganglioside" as used with respect to the present invention include its normal definition in the art (such as that defined above) as well as active fragments thereof.

The ganglioside can be made synthetically or isolated from natural sources. Alternatively, it can be obtained from commercial sources.

The term "ganglioside associated activity" includes any one or more of modulating or immunomodulating a ganglioside receptor, modulating any signalling event prior to, during or subsequent to ganglioside receptor binding.

The term "Ctx" refers to the cholera toxin and CtxB refers to the B subunit of the cholera toxin. In other texts, these may sometimes be identified as CT or Ct or CTB or CtB respectively.

The term "Etx" herein means the *E. coli* heat labile enterotoxin and EtxB is the B subunit of Etx. In other texts, these may sometimes be identified as LT or Lt and LTB or LtB respectively.

The term "adjuvant" includes a substance that enhances an immune response to an antigen.

The term "mucosal adjuvant" includes an agent which is delivered mucosally with an unrelated antigen, such that the agent is capable of facilitating a mucosal immune response to the unrelated antigen. In this way, the agent acts as a so-called mucosal adjuvant.

The term "mucosal surfaces" includes but is not limited to oral, sublingual, intranasal, vaginal, rectal, salivary, intestinal and conjunctival surfaces.

The term "mucosal membrane" and/or "mucosal tissue" includes but is not limited to the intestine, the lung, the mouth, the genital tract, the nose and the eye.

A "vaccine carrier" includes a carrier of relevant antigens (Szostak et a/1996 J Biotechnol 44: 161-170)

The term "mucosal immunogen" includes an agent administerable by a mucosal route that has the capability to evoke local and/or systemic antibody production and/or cell mediated immune reactions and/or delayed type hypersensitivity reactions.

A "hapten" means a small molecule which can act as an epitope but is incapable by itself of eliciting an antibody response.

The term "immunological or oral tolerance" means a reduction in immunological reactivity of a host towards a specific tolerated antigen(s). Immunological or oral tolerance may not mean a complete suppression of the immune response to a particular antigen but it is a form or tolerance also known as "immune deviation" or "split tolerance".

The term "immune deviation" or "split tolerance" can be used to describe the likely preservation of local IgA responses with the retention of some IgG responses but with the down regulation of delayed hypersensitivity and/or IgE responses.

The term "tolerance" means a state of specific immunological unresponsiveness.

A "tolerogen" means a tolerated antigen.

The term "autoimmunity" is used to describe the process by which the body generates an immune response to self-antigens.

The term "agent capable of modulating a ganglioside associated activity" can be used to describe any agent which acts as an immunomodulator through interacting with a ganglioside.

The term "GM1 binding agent" includes any agent which acts as an immunomodulator through interacting with a GM1 ganglioside receptor.

The term "immunomodulator" includes any agent that alters the extent of the immune response to an antigen, by altering the antigenicity of the antigen or by altering in a nonspecific manner the specific reactivity or the nonspecific effector associated mechanisms of the host.

The term "administered" includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors. Non-viral delivery mechanisms include lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "co-administered" means that the site and time of administration of each of the agent and the antigen are such that the necessary modulation of the immune system is achieved. Thus, whilst the agent and the antigen may be administered at the same moment in time and at the same site, there may be advantages in administering the agent at a different time and to a different site from the antigen. The agent and antigen may even be delivered in the same delivery vehicle (such as Macrosol™—see WO95/13795 and WO96/14871)—but with the proviso that the agent and the antigen are uncoupled.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

The term "systemic immunisation" means the introduction of an antigen into a non-mucosal tissue such as the skin or the blood.

The term "self antigens" means components derived from host tissues.

The term "target interaction components" includes but is not limited to an agent capable of modulating a ganglioside associated activity, a ganglioside and/or an antigen.

The term "coupled"—which is synonymous with the term "linked"—means the linkage of the agent with the antigen—which includes but is not limited to direct linkage (such as by an ionic or covalent bond) or indirect linkage by the provision of suitable spacer groups.

The term "uncoupled"—which is synonymous with the term "unlinked"—means that the agent is not coupled to the antigen.

However, in accordance with the present invention, the agent and/or antigen can be coupled to another entity.

The term "affect" includes modulation, such as treatment, prevention, suppression, alleviation, restoration or other alteration of pre-existing condition and/or to potentially affect a future condition, as well as any combination thereof.

An "antigen" means an agent which, when introduced into an immunocompetent animal, stimulates the production of a specific antibody or antibodies that can combine with the agent. The antigen may be a pure substance, a mixture of substance or soluble or particulate material (including cells or cell fragments). In this sense, the term includes any suitable antigenic determinant, auto-antigen, self-antigen, tolerogen, allergen, hapten, and immunogen, or parts thereof, as well as any combination thereof, and these terms are used interchangeably throughout the text.

An "allergen" includes any antigen that stimulates an allergic reaction, inducing a Type I hypersensitivity reaction.

Examples of common allergen sources are outlined in the Table below.

| Group | Examples of Allergens |
|---|---|
| Airborne | |
| grass pollens | ragweed, rye, couch, wild oat, timothy, Bermuda, Kentucky blue, mugwort |
| tree pollens | alder, birch, hazel, beech, Cupressae, oak, olive |
| moulds | *Aspergillus* spp., *Cladosporium* spp., *Alternaria* spp., Basidospores, Ascomycetes |
| cereal grains | wheat, rye, oat |
| animal dander and urine | cat, dog, horse, rabbit, guinea pig, hamster |
| bird feathers | budgerigar, parrot, pigeon, duck, chicken |
| house dust mite | *Dermatophagoides pteronyssinus*, *D. farinae*, *Euroglyphus maynei* |
| insects | cockroach, fly, locust, midge |
| Oral | |
| foods | seafood, legumes, peanuts, nuts, cereals, dairy products, eggs, fruits, tomatoes, mushrooms, alcoholic beverages, coffee, chocolate |
| drugs | penicillins, sulphonamides and other antibiotics, sulphasalazine, carbamazepine |
| Injected | |
| insects | bee and wasp stings, ant and mosquito bites |
| drugs | blood products, sera, vaccines, contrast media, drugs (including anti-asthma drugs and antibiotics) |

The term "allergic condition" includes but is not limited to asthma, allergic cough, allergic rhinitis and conjunctivitis, atopic eczema and dermatitis, uticaria, hives, insect bite allergy, dietary allergy (peanut, fish milk, wheat etc) and drug allergies The term "hypersensitivity condition" includes but is not limited to conditions such as contact hypersensitivity induced by plant poison ivy.

The term "agent" includes entities capable of modulating a ganglioside associated activity. The agent can be one or more of an inorganic or organic chemical, as well as combinations thereof. By way of example the agent can be a polypeptide as well as a variant/homologue/derivative/fragment thereof so long as they retain the required immunomodulatory activity. It also includes mimics and equivalents and mutants thereof. Other agents for the treatment of allergic conditions or hypersensitivity conditions include antibodies to the target interaction components. Such antibodies include, but are not limited to, polyclonal, monoclonal, chimeric, single chain, Fab fragments, fragments produced by a Fab expression library and specifically designed humanised monoclonal antibodies.

Agents capable of modulating a ganglioside associated activity may be designed and produced as outlined above, by methods which are known in the art. By way of example, when the agent of the invention is a protein such as the EtxB subunit or the CtxB subunit, it may be produced, for use in all aspects of this invention by a method in which the gene or genes coding for the specific polypeptide chain (or chains) from which the protein is formed, is inserted into a suitable vector and then used to transfect a suitable host. For example, the gene coding for the polypeptide chain from which the EtxB assemble may be inserted into, for example, plasmid pMM68, which is then used to transfect host cells, such as *Vibrio* sp.60. The protein is purified and isolated in a manner known per se. Mutant genes expressing active mutant EtxB protein may then be produced by known methods from the wild type gene.

Where a target interaction component is a protein, procedures well known in the art may be used for the production of antibodies to that component.

For the production of antibodies, various hosts including goats, rabbits, rats, mice, etc. may be immunized by injection with the target interaction component or any derivative or homologue thereof or oligopeptide which retains immunogenic properties. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, and dinitrophenol. BCG (*Bacilli* Calmette-Guerin) and *Corynebacterium parvum* are potentially useful human adjuvants.

Where a target interaction component is a protein, monoclonal antibodies to that component may be prepared using any technique which provides for the production of antibody molecules by continuous cell lines in culture. These include, but are not limited to, the hybridoma technique originally described by Koehler and Milstein (1975 Nature 256:495-497), the human B-cell hybridoma technique (Kosbor et al (1983) Immunol Today 4:72; Cote et al (1983) Proc Natl Acad Sci 80:2026-2030) and the EBV-hybridoma technique (Cole et al (1985) Monoclonal Antibodies and Cancer Therapy, Alan R Liss Inc, pp 77-96). In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851-6855; Neuberger et al (1984) Nature 312:604-608; Takeda et al (1985) Nature 314:452-454). Alternatively, techniques described for the production of single chain antibodies (U.S. Pat. No. 4,946,779) can be adapted to produce target interaction component specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833-3837), and Winter G and Milstein C (1991; Nature 349:293-299).

Antibody fragments which contain specific binding sites for a target interaction components may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse W D et al (1989) Science 256:1275-128 1).

The target interaction components of the present invention or a derivative or homologue thereof and/or a cell line that expresses the target interaction components of the present invention or a derivative or homologue thereof may be used to screen for antibodies, peptides, or other agent, such as organic or inorganic molecules, that act as modulators of the target interaction, thereby identifying a therapeutic agent capable of modulating the target interaction. For example, antibodies capable of modulating the target interaction may be identified.

Alternatively, screening of peptide libraries or organic libraries made by combinatorial chemistry with recombinantly expressed target interaction components or a derivative or homologue thereof or cell lines expressing the target interaction components or a derivative or homologue thereof may be useful for identification of therapeutic agents that function by modulating the target interaction. Synthetic compounds, natural products, and other sources of potentially biologically active materials can be screened in a number of ways deemed to be routine to those of skill in the art.

A target interaction component polypeptide, its immunogenic fragments or oligopeptides thereof can be used for screening therapeutic compounds in any of a variety of drug screening techniques. The polypeptide employed in such a test may be free in solution, affixed to a solid support, borne on a cell surface, or located intracellularly. The abolition of activity or the formation of binding complexes between the target interaction component and the agent being tested may be measured.

Alternatively, phage display can be employed in the identification of candidate agents which affect the target interaction components.

Phage display is a protocol of molecular screening which utilises recombinant bacteriophage. The technology involves transforming bacteriophage with a gene that encodes an appropriate ligand (in this case a candidate agent) capable of reacting with a target interaction component (or a derivative or homologue thereof) or the nucleotide sequence (or a derivative or homologue thereof) encoding same. The transformed bacteriophage (which preferably is tethered to a solid support) expresses the appropriate ligand (such as the candidate agent) and displays it on their phage coat. The entity or entities (such as cells) bearing the target molecules which recognises the candidate agent are isolated and amplified. The successful candidate agents are then characterised. Phage display has advantages over standard affinity ligand screening technologies. The phage surface displays the candidate agent in a three dimensional configuration, more closely resembling its naturally occurring conformation. This allows for more specific and higher affinity binding for screening purposes.

Accordingly, the present invention provides a method for screening a plurality of agents for specific binding affinity with the target interaction component or a derivative or homologue thereof comprising providing a plurality of agents; combining the target interaction components or a derivative or homologue thereof with each of a plurality of agents for a time sufficient to allow binding under suitable conditions; and detecting binding of the target interaction components, or a derivative or homologue thereof to each of the plurality of agents, thereby identifying the agent or agents which specifically bind the target interaction components. In such an assay, the plurality of agents may be produced by combinatorial chemistry techniques known to those of skill in the art.

Another technique for screening provides for high throughput screening of agents having suitable binding affinity to the target interaction components polypeptides and is based upon the method described in detail in WO 84/03564. In summary, large numbers of different small peptide test compounds are synthesized on a solid substrate, such as plastic pins or some other surface. The peptide test agents are reacted with the target interaction component fragments and washed. A bound target interaction component is then detected—such as by appropriately adapting methods well known in the art. A purified target interaction component can also be coated directly onto plates for use in the aforementioned drug screening techniques. Alternatively, non-neutralizing antibodies can be used to capture the peptide and immobilize it on a solid support.

The present invention also provides a pharmaceutical composition for treating a subject in need of same comprising administering a therapeutically effective amount of an agent capable of modulating a ganglioside associated activity and a pharmaceutically acceptable carrier, diluent, excipient or adjuvant.

The pharmaceutical compositions may be for human or animal usage and will typically comprise any one or more of a pharmaceutically acceptable diluent, carrier, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

The pharmaceutical composition may be formulated together with an appropriate antigen.

Alternatively, a kit may be provided comprising separate compositions for each of the therapeutic agent and the antigen.

In some embodiments of the present invention, the pharmaceutical compositions will comprise one or more of: an agent that has been screened by an assay of the present invention; wherein the agent is capable of modulating a ganglioside associated activity The present invention also relates to pharmaceutical compositions comprising effective amounts of antigen in admixture with a pharmaceutically acceptable diluent, carrier, excipient or adjuvant (including combinations thereof).

The present invention also provides a method of treating a subject in need of same comprising administering to said subject an effective amount of the pharmaceutical composition of the present invention.

The present invention relates to pharmaceutical compositions which may comprise all or portions of the target interaction components alone or in combination with at least one other agent, such as a stabilizing compound, and may be administered in any sterile, biocompatible pharmaceutical carrier, including, but not limited to, saline, buffered saline, dextrose, and water.

There may be different composition/formulation requirements dependent on the different delivery systems.

The pharmaceutical composition of the present invention may be formulated to be delivered by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is delivered mucosally through the gastrointestinal mucosa, it is preferably stable during transit though the gastrointestinal tract; for example, it is preferably resistant to proteolytic degradation, stable at acid pH and resistant to the detergent effects of bile.

Typically, a physician will determine the actual dosage which will be most suitable for a subject and it will vary with the age, weight and response of the particular subject. While a single dose of the agent and the antigenic determinant may be satisfactory, multiple doses are contemplated within the scope of the invention.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

There may be different delivery requirements dependent on the different composition/formulation systems.

Expression vectors derived from retroviruses, adenovirus, herpes or vaccinia viruses, or from various bacterial plasmids, may be used for delivery of the agent to the targeted tissue and/or cell population. Methods which are well known to those skilled in the art can be used to construct recombinant vectors containing the agent. Alternatively, the agent can be delivered to target cells in liposomes.

By way of example, the controlled release of antigens on mucosal surfaces using biodegradable polymer microspheres may help to target antigens and reduce the numbers of doses required for primary immunisation (Gupta and Siber 1995 Vaccine 13: 1263-1276).

Encapsulation of vaccines in biodegradable microspheres provides excellent mucosal immunogens. Recombinant Norwalk Virus-like (rNV) particles may also be used for mucosal antigen delivery (Ball et al 1996 Arch Virol Suppl 12: 243-249).

Viral Like Particles (VLPs) have been utilised as vaccine delivery system for multiple immunogens including B and T cell epitopes (Roy 1996 Intervirology 39: 62-71).

One preferred method of oral delivery uses formations as described in WO95/13795, WO96/17593 and WO96/17594. These formulations allow macromolecules such as proteins to be solubilised in "oils" for oral delivery. Such formulations therefore allow delivery of the macromolecules to mucosal surfaces in the gut.

In a further approach, again when the therapeutic agent is a protein, it is possible to deliver such proteins by means of a bacterial delivery system such as that described in WO 93/17117. This system utilises the bacterium *Lactococcus* lactis to deliver proteins, for instance orally or indeed by other mucosol routes such as nasally.

In summary, the present invention provides the use of an agent in the manufacture of a medicament to affect an allergic condition and/or a hypersensitive condition; wherein the agent is capable of modulating a ganglioside associated activity wherein the agent is not coupled with an antigen.

In another broad aspect, the present invention provides an immunological tolerance inducing agent comprising an agent capable of modulating a ganglioside associated activity which is not coupled to an antigen.

Other aspects of the present invention are now presented below by way of numbered paragraphs, which include:

1. The use of an agent having GM1 binding activity, or an agent having an effect on GM1 mediated intracellular signalling events, but no GM1 binding activity, in the preparation of a medicament to treat an allergic or other hypersensitive condition, with the proviso that said agent is not coupled with an allergen and/or an antigen.
2. The use as defined in paragraph 1 wherein the agent is a GM1 binding agent such as Ctx, Etx, CtxB or EtxB or a mutant form or derivative thereof.
3. The use as defined in paragraph 1 and paragraph 2 wherein the medicament is for the prophylaxis or treatment of asthma, allergic cough, allergic rhinitis, conjunctivitis, atopic eczema, dermatitis, uticaria, hives, insect bite allergy, dietary allergy (peanut, fish, milk, wheat etc), drug allergies or contact and other hypersensitivities.
4. A method for the treatment or prophylaxis of an allergic or other hypersensitive condition which comprises administering to a subject an effective amount of an agent having GM1 binding activity, or an agent having an effect on GM1 mediated intracellular signalling events, but no GM1 binding activity, with the proviso that said agent is not coupled with an allergen and/or an antigen.
5. A method as defined in paragraph 4 wherein the agent is a GM1 binding agent such as Ctx, Etx, CtxB or EtxB or a mutant form or derivative thereof.
6. A method as defined in paragraph 4 or paragraph 5 wherein the method is for the prophylaxis or treatment of asthma, allergic cough, allergic rhinitis, conjunctivitis, atopic eczema, dermatitis, uticaria, hives, insect bite allergy, dietary allergy (peanut, fish, milk, wheat etc), drug allergies or contact hypersensitivity.
7. A pharmaceutical composition for the treatment of a human allergic and/or hypersensitivity disease comprising
   (i) an agent having GM1 binding activity; or
   (ii) an agent having an effect on GM1 mediated intracellular signalling events, but no GM1 binding activity;
with the proviso that the agent is not coupled with an allergen/antigen; and a pharmaceutically acceptable carrier or diluent therefor.
8. A product comprising an agent having GM1 binding activity, or an agent having an effect on GM1 mediated intracellular signalling events, but no GM1 binding activity, in the preparation of a medicament to treat an allergic or other hypersensitive condition, with the proviso that said agent is not coupled with an allergen and/or an antigen, and at least one antigen/allergen as a combined preparation for simultaneous, separate or sequential use.

The present invention will now be described only by way of example.

EXAMPLES

Screens for Agents Capable of Modulating Ganglioside Associated Activity

Agents capable of modulating ganglioside associated activity are tested by any one of a variety of methods.

Examples of such methods include, but are not limited to the following methods:

1. Binding to a ganglioside receptor, such as GM1, is determined by using purified GM1 to coat microtiter plates. Following blocking of further non-specific protein binding to the plate, the agent under investigation is applied to the plate and allowed to interact prior to washing and detection with specific antibodies to said agent. Conjugation of the antibodies either directly or indirectly to an enzyme or radiolabel allows subsequent quantification of binding either using colormetric or radioactivity based methods (ELISA or RIA respectively).
2. The pentasaccharide moiety of a ganglioside, such as GM1, is bound to a suitable column matrix in order to allow standard affinity chromatography to be performed. Removal of known compounds applied to the column from the diluent are used as evidence for binding activity. Alternatively, where mixtures of compounds are applied to the column, elution and subsequent analysis allows the properties of the agent capable of modulating ganglioside associated activity to be determined.

Protein analysis includes peptide sequencing and tryptic digest mapping followed by comparisons with available databases. If eluted proteins cannot be identified in this way, then standard biochemical analysis, such as, for example, mass determination by laser desorption mass spectrometry is used to further characterise the compound. Non-proteins eluted from GM1-affinity columns are analysed by HPLC and mass spectrometry of single homogenous peaks.

3. The ability to bind to gangliosides, such as GM1, and the precise affinity of the interaction may be determined using plasmon surface resonance as previously reported [Kuziemko et al (1996) Biochem 35:6375-6384].

Evaluation of Identified Agents

The identification of agents capable of modulating ganglioside associated activity such that the modulation of the ganglioside associated activity affects an allergic condition and/or a hypersensitivity condition is determined as follows:

Laboratory animals are stimulated to produce antigen-specific IgE by methods well known in the art. By way of example, mice are challenged with alum precipitated soluble protein antigen (e.g. ovalbumin or allergens known to be involved in human allergic diseases such as ragweed or house dust mite antigens) either subcutaneously or intraperitoneally.

In the unmanipulated animal, this procedure routinely leads to the production of antigen-specific IgE which is easily detected in the serum, by standard ELISAs, using the antigen to coat suitable microtiter plates. Serum from the immunised mice is applied to the plates after non-specific protein binding has been blocked and the presence of IgE is determined using widely available labelled antibodies specific for murine IgE.

In order to screen agents for their capability to prevent or treat allergy, agents capable of modulating ganglioside associated activity are administered to mice either in the presence or absence of the challenge antigen at a range of doses, and by a variety of routes. Although the oral route is the preferred method of administration, delivery can be by other mucosal surfaces or parenterally. The frequency of such administration as well as the timing of repetitive dosing is also investigated. Such intervention strategies are utilised either prior to the IgE inducing antigen challenge (prophylaxis) or after the IgE inducing antigen challenge (treatment). Antigen challenge can be either with (i) the antigen used as part of the prophylactic or treatment protocol; (ii) an unrelated antigen or (iii) a mixture of the challenge and unrelated antigen in order to test the specificity of the response and the induction of bystander suppression respectively.

Efficacy is determined in a variety of ways and is manifested as a number of different outcomes.

1. Antigen-specific IgE levels. Measurement of serum IgE by specific ELISA (as described) is used to determine whether prophylactic or treatment protocols are capable of reducing levels of serum antigen-specific IgE. Other methods known in the art for the determination of IgE response are used either as alternatives to ELISA or in order to provide complementary data. Such methods include the so-called "Using Chamber test" or "passive cutaneous anaphylaxis" assay. A reduction in specific IgE, as determined by any of these assays, is a strong marker of potential clinical efficacy.

2. Antigen specific T-cell reactivity. The responses of T-cells, derived from secondary lymphoid organs of the treated animals to the challenge antigen, is investigated using established methodology. Cell suspensions are prepared and cultured, in the presence or absence of the challenge antigen. At appropriate time intervals after the initiation of the cultures, samples are assessed for cell proliferation and cytokine production.

Cytokines are measured by specific capture ELISA, by intracellular staining followed by cytometric analysis, by RT-PCR or by other established procedures. Comparison of cell proliferation and cytokine production, in the presence of antigen as opposed to its absence, provides in each case a measure of that part of the response which is specific to the challenge antigen. Evidence of efficacy of prophylactic or treatment protocols is demonstrated by a reduction in the production of Th2 associated cytokines (in particular IL-4) or by an increased expression of cytokines which are involved in down-regulating the allergic response (for example, IL-10 or TGFβ).

3. IgG and IgA levels. Protocols which do not reduce the levels of antigen specific IgE can still be considered as potentially effective in the event that they are also able to enhance the production of other non-allergy associated antibody isotypes. Thus investigation of serum and mucosal secretions from animals which have been either untreated or given agents under investigation as part of prophylactic or treatment protocols for the presence of IgG and IgA are also carried out. Standard antigen specific ELISA assays (as described) utilising detecting antibodies specific for IgG and specific subclass thereof, and IgA are used for this purpose. Enhanced production of secreted or serum IgG or IgA antibodies indicate efficacy since such antibodies can be expected to prevent an allergen from cross-linking IgE bound to mast cells, basophils and cosinophils or limit the uptake of antigen across the mucosal epithelium and hence prevent the subsequent allergic inflammatory response.

Enzyme Linked Immunosorbent Assays (ELISAs)

Binding of EtxB or EtxB (G33D) to GM1 is examined by a GM1-ELISA (Amin, T., & Hirst, T. R. (1994) Prot. Express. and Purif. 5, 198-204).

Sera and gut secretions are examined for the presence of anti-B subunit IgG and IgA antibodies by ELISAs in which samples are applied to microtitre plates (Immulon I, Dynateck, USA) coated with 5 µg/ml of either EtxB or EtxB (G33D) in PBS. Anti-B subunits IgA antibodies in gut secretion supernatants are extrapolated from a standard curve made by coating 2 rows of wells on each plate with 1 µg/ml rabbit anti-mouse IgA (a chain specific; Zymed Lab, USA) in PBS followed by addition of 1 µg/ml of mouse myeloma IgA (MOPC 315, Sigma, USA). To measure total IgA, wells are coated with rabbit anti-mouse IgA followed by addition of gut secretion supernatants. All samples are serially diluted. Goat anti-mouse IgG (Fc fragment specific; Jackson Lab., USA) or goat anti-mouse IgA (a chain specific; Sigma) peroxidase conjugate are diluted and added to all wells. The anti-B subunit IgG titer, giving an $A_{450mm} \geqq 0.2$, is determined. The IgA anti-B subunit response for each of EtxB and EtxB (G33D) in gut secretions is calculated as "IgA specific activity" [mean IgA anti-B subunit (µg/ml)/total IgA (µg/ml)].

A known ELISA method for measuring cytokine levels of IL-2, IL-4, IL-5, IL-10 and IFN-γ is used. Briefly, microtiter plates are coated with rat antibodies to mouse IL-2, IL-4, IL-5, IL-10 and IFN-γ. Plates are blocked with 2% (w/v) bovine serum albumin. Supernatants from culture medium are added to wells and diluted down. One row on each plate for each cytokine contains a standard amount of recombinant cytokines. Plates are then incubated with 0.5 µg/ml of biotinylated anti-cytokine monoclonal antibodies followed by addition of avidine-peroxidase and 3,3',5,5'-Tetramethylbenzidene (TMB) substrate and read at $A_{450nm}$.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method for treatment of respiratory allergy in a subject in need thereof comprising administering to the subject an effective amount of an agent wherein the agent is *E. coli* heat-labile enterotoxin B subunit (EtxB) that binds to GM1.

2. The method according to claim 1, wherein the respiratory allergy is allergic rhinitis.

3. The method according to claim 1, wherein EtxB is administered mucosally, intravenously, intramuscularly, subcutaneously or intranasally.

4. The method according to claim 3, wherein EtxB is administered intranasally.

* * * * *